(12) United States Patent
Mackin

(10) Patent No.: US 6,408,203 B2
(45) Date of Patent: Jun. 18, 2002

(54) APPARATUS AND METHOD FOR CONTEMPORANEOUS TREATMENT AND FLUOROSCOPIC MAPPING OF BODY TISSUE

(76) Inventor: Robert A. Mackin, 1033 Lake Way Point, Flagstaff, AZ (US) 86004

( * ) Notice: Subject to any disclaimer, the term of this patent is extended or adjusted under 35 U.S.C. 154(b) by 0 days.

(21) Appl. No.: 09/797,125

(22) Filed: Feb. 27, 2001

Related U.S. Application Data

(63) Continuation of application No. 09/213,778, filed on Dec. 17, 1998, now Pat. No. 6,193,763.

(51) Int. Cl.[7] ................................. A61B 5/05
(52) U.S. Cl. ..................................... 600/433
(58) Field of Search ............................ 604/21; 600/427, 600/431, 433

(56) References Cited

U.S. PATENT DOCUMENTS

| | | | |
|---|---|---|---|
| 3,822,702 A | 7/1974 | Bolduc et al. | 128/235 |
| 3,833,003 A | 9/1974 | Taricco | 128/347 |
| 4,784,133 A | 11/1988 | Mackin | 128/303.1 |
| 4,861,330 A | 8/1989 | Voss | 600/18 |
| 4,976,710 A | 12/1990 | Mackin | 606/15 |
| 5,312,341 A | 5/1994 | Turi | 604/96 |
| 5,427,097 A | * 6/1995 | Depp | 600/427 |
| 5,568,809 A | * 10/1996 | Ben-haim | 600/433 |
| 5,722,403 A | 3/1998 | McGee et al. | 128/642 |
| 5,725,521 A | 3/1998 | Mueller | 606/7 |
| 5,725,523 A | 3/1998 | Mueller | 606/15 |
| 5,769,812 A | 6/1998 | Stevens et al. | 604/4 |

FOREIGN PATENT DOCUMENTS

| | | | |
|---|---|---|---|
| EP | 0283661 | 9/1988 | 604/96 |
| GB | 2017506 | 10/1979 | 606/15 |

* cited by examiner

Primary Examiner—William E. Kamm
(74) Attorney, Agent, or Firm—Cahill, Sutton & Thomas P.L.C.

(57) ABSTRACT

An apparatus for contemporaneously treating a sequence of treatment sites in an internal organ and creating a viewable map of the treated sites includes a first catheter having a proximal end and a distal end for insertion through a body passage to tissue needing treatment. A needle assembly is attached to the distal end of the first catheter to permit injection of fluid into treatments sites of the tissue. A fluid injection assembly is connected to the proximal end of the first catheter and containing predetermined amounts of radiographic contrast agent and treatment agent for injection into the various treatment sites. A radiographic visualizing apparatus is aimed at the treatment sites, including a display screen for displaying the extent of migration of radiographic contrast agent around each treatment site after injection, so that a radiographic marking appears on the display screen for a predetermined amount of time after each injection, showing which treatment sites have been treated. In another embodiment a second catheter having a distal end with a treatment element attached to its distal end and a control apparatus attached to its proximal end is used to perform treatment of the tissue contemporaneously with injection of radiographic contrast agent into the tissue.

3 Claims, 3 Drawing Sheets

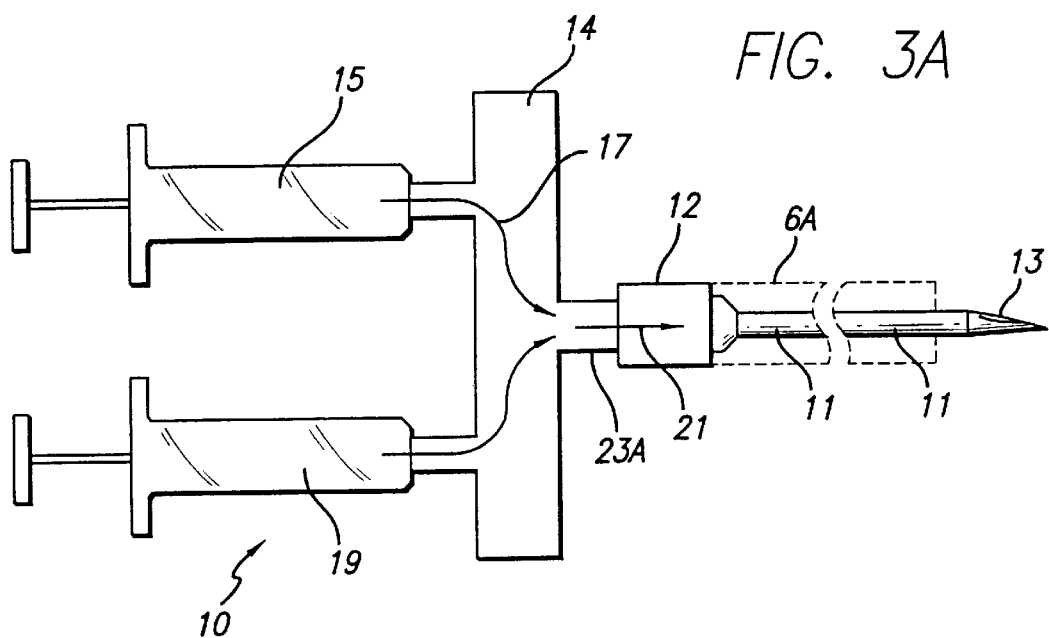
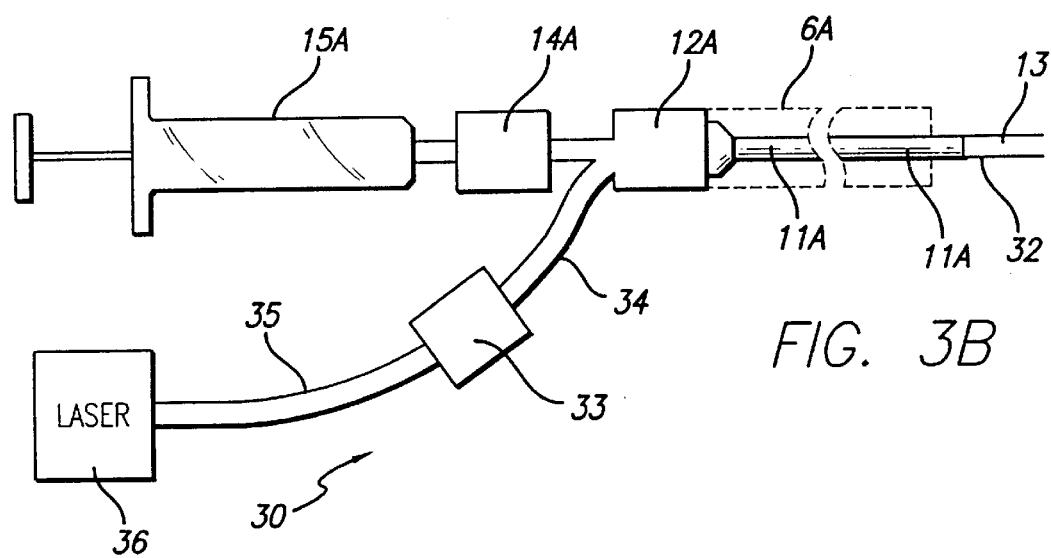
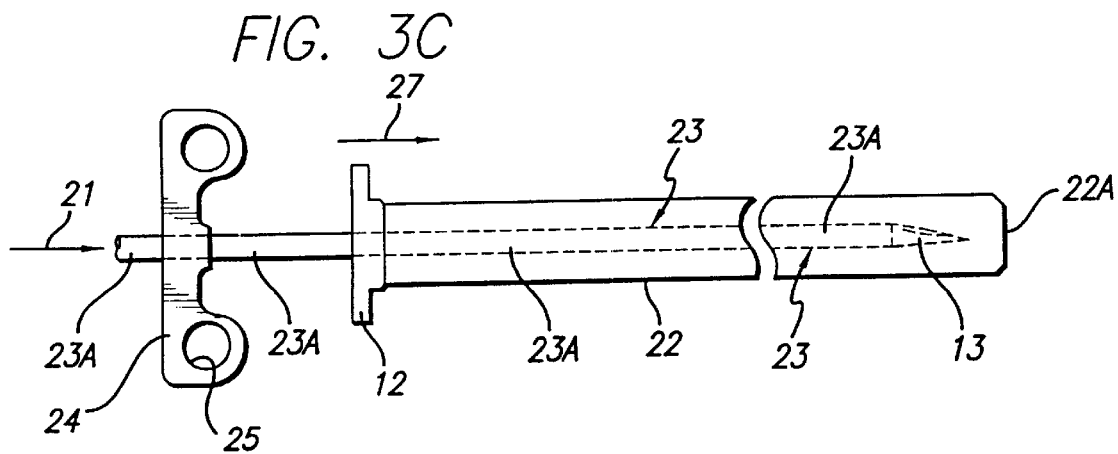

APPARATUS AND METHOD FOR CONTEMPORANEOUS TREATMENT AND FLUOROSCOPIC MAPPING OF BODY TISSUE

This application is a continuation of application Ser. No. 09/213,778, filed Dec. 17, 1998, and issued Feb. 27, 2001 as U.S. Pat. No. 6,193,763.

BACKGROUND OF THE INVENTION

The invention relates to an apparatus and technique for treatment and fluoroscopic mapping of treated tissue by injection of radiographic contrast agent into the tissue and contemporaneous treatment of the same tissue to provide a radiographic visual map of treated locations. The invention also relates to use of such apparatus and technique to promote revascularization of heart muscle/tissue.

Recent research and investigation suggests that part of the process of healing wounds in human tissue is dependent on blood vessel growth, which is believed to be in turn dependent on release of angiogenesis or blood vessel growth factors by the ischemic (or injured) tissue. It has been suggested at a recent conference on angiogenesis and direct myocardial revascularization that any method, i.e., laser, radio frequency electromagnetic signals, or other technique that results in myocardial tissue ischemia (or injury) may result in release of angiogenesis growth factors and development of blood vessel growth and blood flow to the ischemic/injured area. (As used herein, the term "ischemic" is intended to refer to reversible tissue damage and the term "injury" is intended to refer to irreversible tissue damage.)

While there are publications of references that disclose dyeing tissue of the heart during direct open heart surgery to mark lased or otherwise treated sites thereof, and although there are prior references disclosing introduction of radiographic contrast agent into various organs such as the chambers of the heart or coronary arteries for the purpose of radiographic imaging of the contractions of the heart, the prior art does not disclose use of needles or other means installed on distal ends of catheters to inject radiographic contrast agents into heart muscle or other tissue. In fact, in prior practice injection of radiographic contrast agent directly into tissue is deliberately avoided. However, angiogenesis factors alone have been injected into heart muscle tissue.

My patent U.S. Pat. No. 4,976,710 entitled "WORKING WELL BALLOON METHOD", issued Dec. 11, 1990, incorporated herein by reference, discloses a working well balloon catheter and method for visualizing and performing procedures on the inner myocardial wall.

There is an unmet need for an improved apparatus and technique for performing medical procedures on tissue within the body, especially within the heart, and repetitively radiographically marking contemporaneously treated sites so the physician can avoid multiple treatments of the same areas, to avoid complications such as perforation of the heart, to facilitate completion of a procedure to decrease radiation exposure of the patients, and to reduce overall costs by providing a more efficient method of treatment. In contrast, conventional radiography does not provide a way to determine if an internal area already has been subjected to contemporaneous treatment.

SUMMARY OF THE INVENTION

Accordingly, it is an object of the invention to provide an apparatus and technique for repetitively effectively treating and effectively marking treated sites within an internal organ.

It is another object of the invention to provide an apparatus and technique to promote safe, rapid and effective marking and revascularization of internal organs such as the heart.

It is another object of the invention to provide an apparatus and technique to contemporaneously mark and reduce harmful vascularization in tumorous tissue.

It is another object of the invention to provide an apparatus and technique for reducing or avoiding the need to perform bypass surgery.

It is another object of the invention to provide an apparatus and method for reducing or avoiding the need to perform an angioplasty procedure.

Briefly described, and in accordance with one embodiment thereof, the invention provides an apparatus for contemporaneously treating a sequence of treatment sites in an internal organ and creating a viewable map of the treated sites, including a first catheter having a proximal end and a distal end for insertion through a body passage to tissue needing treatment. A needle assembly is attached to the distal end of the first catheter to permit injection of fluid into treatments sites of the tissue. A fluid injection assembly is connected to the proximal end of the first catheter and containing a predetermined fluid mixture of radiographic contrast agent and treatment substance for injection into the various treatment sites. A fluoroscopic visualization apparatus is aimed at the treatment sites, including a display screen for displaying the extent of radiographic contrast agent around each treatment site after injection. Radiographic markings appear on the display screen for a predetermined amount of time after each injection showing which treatment sites have been treated. In one embodiment a guide wire is introduced to extend through the body passage to effectuate introducing an outer or sheath catheter through which the first catheter then is passed to the desired treatment site. In one embodiment, a working well balloon is affixed to the distal end of a sheath catheter to abut a wall of the tissue. A second catheter having a distal end with a treatment element, such as a needle, laser lens, biopsy forceps, etc. attached to its distal end and a control apparatus attached to its proximal end can be used for controlling treatment of the tissue contemporaneously with injection of radiographic contrast agent into the tissue.

BRIEF DESCRIPTION OF THE DRAWINGS

FIG. 3A is a diagram of an embodiment of the invention in which a contrast agent and a treatment substance both are introduced through a catheter positioned in an artery and extending into the interior of the heart, and injected through a needle on the distal end of the catheter into the heart muscle.

FIG. 3B is a diagram of a catheter in which radiographic contrast agent is introduced from the proximal end of a catheter extending through an artery and into the interior of the heart, and injected by a distal needle into the heart muscle and the injection site is contemporaneously treated by a laser beam advanced through a fiber within the catheter from a proximal laser source.

FIG. 3C is a diagram of the needle catheter assembly 11 shown in FIG. 3A.

DETAILED DESCRIPTION OF THE PREFERRED EMBODIMENTS

Figure 1:
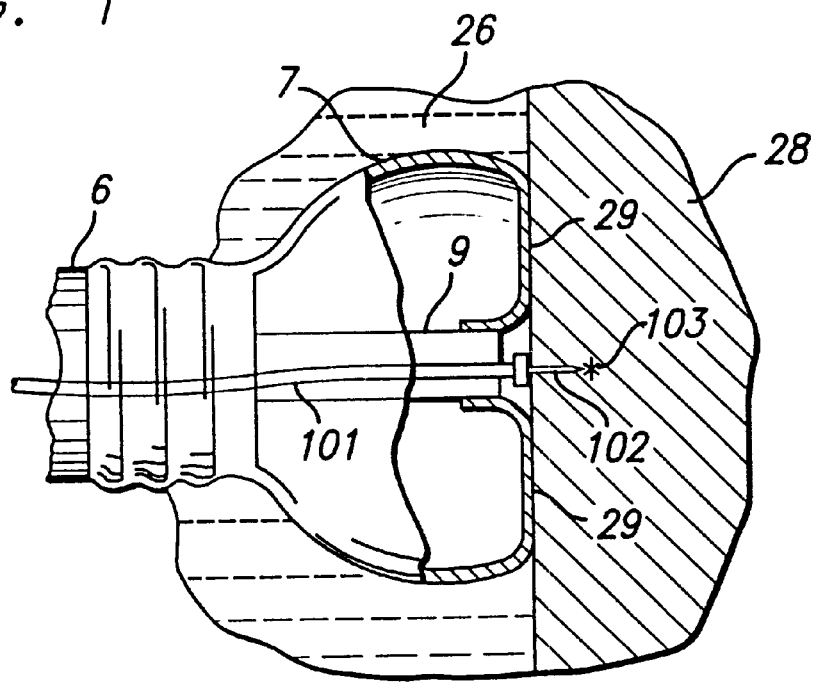
FIG. 1 is a partial section view diagram of a working well balloon catheter pressed against the myocardial wall within a heart, with a needle for injection of radiographic contrast agent into the myocardial tissue.

Referring to FIG. 1, a catheter 101 is inserted through an outer catheter 6 having a working well balloon 7 of the type described in my above referenced patent U.S. Pat. No. 4,976,710. Working well balloon 7 is pressed against the interior of myocardial wall or heart muscle 28. The working well balloon assembly 6, 7 may be introduced through a major artery such as the femoral artery or aorta, as indicated in FIG. 8 of above referenced patent U.S. Pat. No. 4,976,710.

In accordance with one embodiment of the present invention, a needle assembly 102 is provided on the distal end of catheter 101, and a certain amount of radiographic contrast agent is injected into the heart muscle 28. The radiographic contrast agent can, for example, be ISOVIEW or OMNIPAQUE. The amount can be in the range from a fraction of a cc (cubic centimeter) to several cc. The injected contrast agent forms a mark 103 which has the appearance of a large asterisk and remains visible during conventional radiography. After the marking 103 has been formed and the proximate tissue has been contemporaneously treated in some manner, the working well balloon 7 is moved to an adjacent location. (The term "contemporaneous" as used herein is intended to refer to acts which occur at the same time or approximately the same time. For example, acts which occur within a few seconds to a few minutes of each other are considered to be contemporaneous.) The procedure is repeated, and another radiographically viewable marking 103 is produced in the myocardial muscle tissue 28 by injecting the radiographic contrast agent. This process is repeated to create a map of treated tissue locations which are radiographically viewed during the entire procedure. (The term "radiographic" procedure as used herein is intended to include but is not limited to common fluoroscopy.)

The portion of the heart marked in this manner could be a portion of the heart muscle that is not receiving adequate blood supply and nourishment such as oxygen because of a plaque blockage in an artery. In that case it is assumed that the patient may be in need of conventional coronary bypass surgery or a conventional angioplasty procedure (coronary bypass surgery includes insertion of a suitable blood vessel extending from the aorta beyond the plaque blockage to a segment of the blood vessel beyond the blockage) to provide nourishment to myocardial tissue that is being starved as a result of the blockage.

In accordance with one embodiment of the present invention, the amount of radiographic contrast agent injected at each treatment site may be sufficient to cause ischemia/injury in the tissue proximate to each stain spot 103. The ischemia/injury actually can constitute part or all of the contemporaneous treatment, because the ischemia/injury may cause release of angiogenesis factors. Angiogenesis factors or blood vessel growth factors have been shown to induce the development of blood flow within a few days of the onset of the healing process. Within just a few weeks, the previously blood-starved myocardial tissue can become re-vascularized with a network of blood vessels that adequately nourish it, making the coronary bypass operation or an angioplasty procedure unnecessary.

Figure 2:
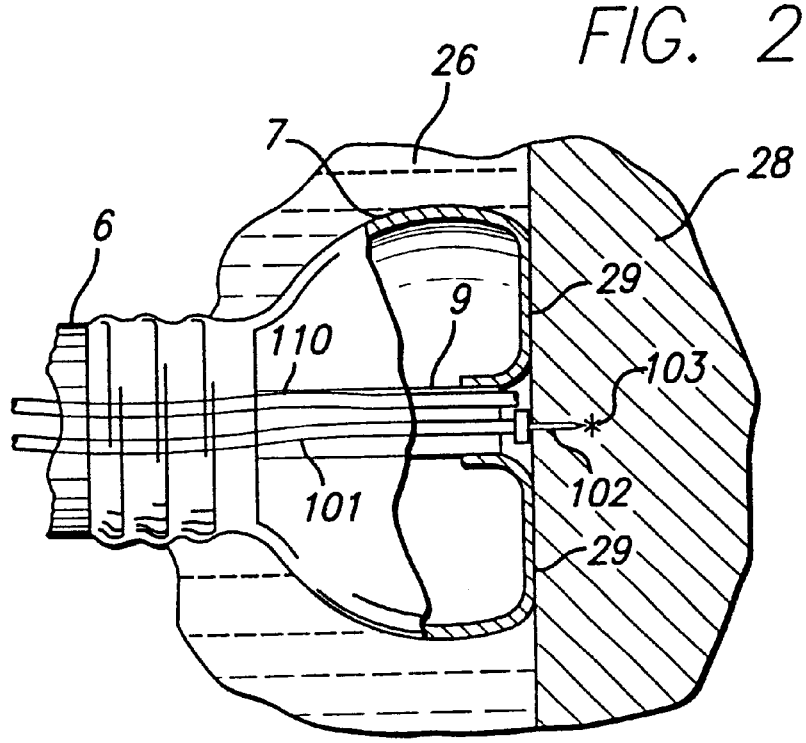
FIG. 2 is a partial section view similar to that of FIG. 1, with an additional catheter for performing a lasing, biopsy, or other medical procedure, with the other catheter being used to contemporaneously inject contrast agent into the myocardial tissue at the treatment site to thereby provide a fluoroscopic treatment map.

FIG. 2 shows a diagram similar to FIG. 1, except that an additional catheter 110 is introduced through the main channel of catheter 6 of the working well balloon assembly. The second catheter 110 can be utilized to perform lasing, chemical injection treatment, biopsy tissue removal, or any of the other treatment procedures mentioned in the above-identified U.S. Pat. No. 4,976,710 patent. Each time such treatment is performed by means of catheter 110, catheter 101 and needle 102 also are used to inject enough radiographic contrast agent to produce a radiographically observable marking 103 at the location of the treatment contemporaneously accomplished by means of the other catheter 110. A map of radiographic markings of the treated areas of the heart is thereby created and observed during the treatment procedure to ensure that all desired portions of the heart tissue are treated, and also to ensure that no portion of the heart tissue is treated more than is necessary.

In accordance with another broader aspect of the method of the present invention, instead of injecting enough of the radiographic contrast agent to cause physical injury of tissue around the point of injection, the injected fluid contains a mixture of (1) a sufficient amount of the radiographic contrast agent to adequately mark the injection site and thereby allow radiographic imaging thereof for a desired period of time, and (2) a suitable amount of a treatment substance. The treatment substance could include angiogenesis factor, or other suitable therapeutic substance. For example, if the tissue being stained is tumorous or cancerous tissue, angiogenesis blocking factors or other caustic or tissue-destructive substances can be injected contemporaneously with the radiographic contrast agent to retard, rather than promote vascularization.

The most basic technique of the invention does not have to be used in conjunction with the working well balloon as described above with reference to FIGS. 1 and 2. In its broadest aspect, the invention simply constitutes (1) use of a catheter and associated distal needle to achieve radiographic marking of selected tissue site by radiographic contrast agent anywhere in the human body, and (2) contemporaneous physical or chemical treatment of the same tissue sites, using the same catheter and/or a different catheter and/or a laser fiber.

Referring to FIG. 3A, a catheter assembly 10 includes a needle catheter assembly 11 introduced, typically through a femoral artery and through the aorta, into a chamber of the heart, for example the left ventricle. Needle catheter assembly 11 (subsequently described with reference to FIG. 3C) normally would be introduced through an outer guide catheter of which is indicated by dashed line 6A. Guide catheter 6A usually would be introduced earlier with aid of a guide wire (not shown) which then is removed. Needle catheter assembly 11 has a retractable needle 13 on its distal end.

Referring to FIG. 3C, needle catheter assembly 11 includes an outer catheter or sheath 22 and a needle catheter 23. Needle catheter 23 includes a catheter tube 23A extending through sheath 22. A locking hub 12 connected to the proximal end of sheath 22 performs the function of locking needle catheter 23 to sheath 22 with needle 13 retracted during introduction of needle catheter assembly 11 through guiding catheter 6A (FIG. 3A). An injection needle 13 is rigidly attached to the distal end of catheter tube 23A. The proximal end of catheter 23A extends through locking hub 12 beyond the proximal end of sheath 22, and opens into the outlet port of subsequently described manifold 14 to receive a flow 21 of fluid being injected from one or both of syringes 15 and 19. The proximal end of catheter tube 23 is engaged by a handpiece 24 having finger eyelets 25 to allow needle catheter 23 to be retracted to a retracted configuration as shown in FIG. 3C and locked to sheath 22 as needle catheter assembly 11 is advanced to the desired site. Then locking hub 12 can be loosened, and handpiece 24 is manipulated to advance needle 13 beyond the distal end 22A of sheath 22 as shown in FIG. 3A into heart muscle or other tissue so that radiographic contrast agent and/or treatment substance can be injected therein. (Needle 13 needs to be retracted during introduction of needle catheter assembly 11 through guide catheter 6A (FIG. 3A) to prevent damage to guiding catheter 6A.)

The proximal end of catheter tube 23A of needle catheter assembly 11 is connected to the outlet port of three port manifold 14. A syringe 15 is in fluid communication with the interior of manifold 14. Syringe 15 contains radiographic contrast agent by means of which the physician can inject radiographic contrast agent through a needle catheter assembly 11 and needle 13 thereof into heart muscle or other tissue of an internal organ.

A second syringe 19 includes treatment substance, for example angiogenesis growth factor, which can be injected through manifold 14 into catheter port 12 contemporaneously with the introduction of the radiographic contrast agent in syringe 15. Usually it would be best to inject the radiographic contrast agent into the heart muscle at the injection site first, and then radiographically visualize the site to be certain that the needle was properly inserted therein, and then introduce the treatment substance from syringe 19 into the injection site, to avoid wasting treatment substance. If the organ or tissue at the injection site were cancerous, the treatment substance could be a growth-blocking substance.

Alternatively, radiographic contrast agent could be mixed with treatment substance and the mixture could be loaded into a single catheter which could then introduce the mixture into the needle catheter assembly 11.

FIG. 3B shows another embodiment of the invention, in which catheter assembly 11A includes both a channel by means of which radiographic contrast agent from a syringe 15A is introduced through a needle 13 of a needle catheter assembly into heart muscle tissue at the injection site. Catheter assembly 11A also includes a second channel through which a laser fiber (or other treatment device) 32 having a distal end adjacent to needle 13 passes from port 12A of catheter assembly 11A, through a catheter 34 and a laser fiber port 33, and through a laser fiber 35 to a laser source (or other control device) 36. The injection of the radiographic contrast agent from syringe 15A can be simultaneous with or contemporaneous with the laser treatment (or other treatment). (Alternatively, block 36 could contain a mechanism for control of a radio frequency energy delivery device, a biopsy forceps catheter, or other device introduced through ports 33 and 12A into catheter 11A, to allow treatment of tissue at the injection site.)

Figure 4:
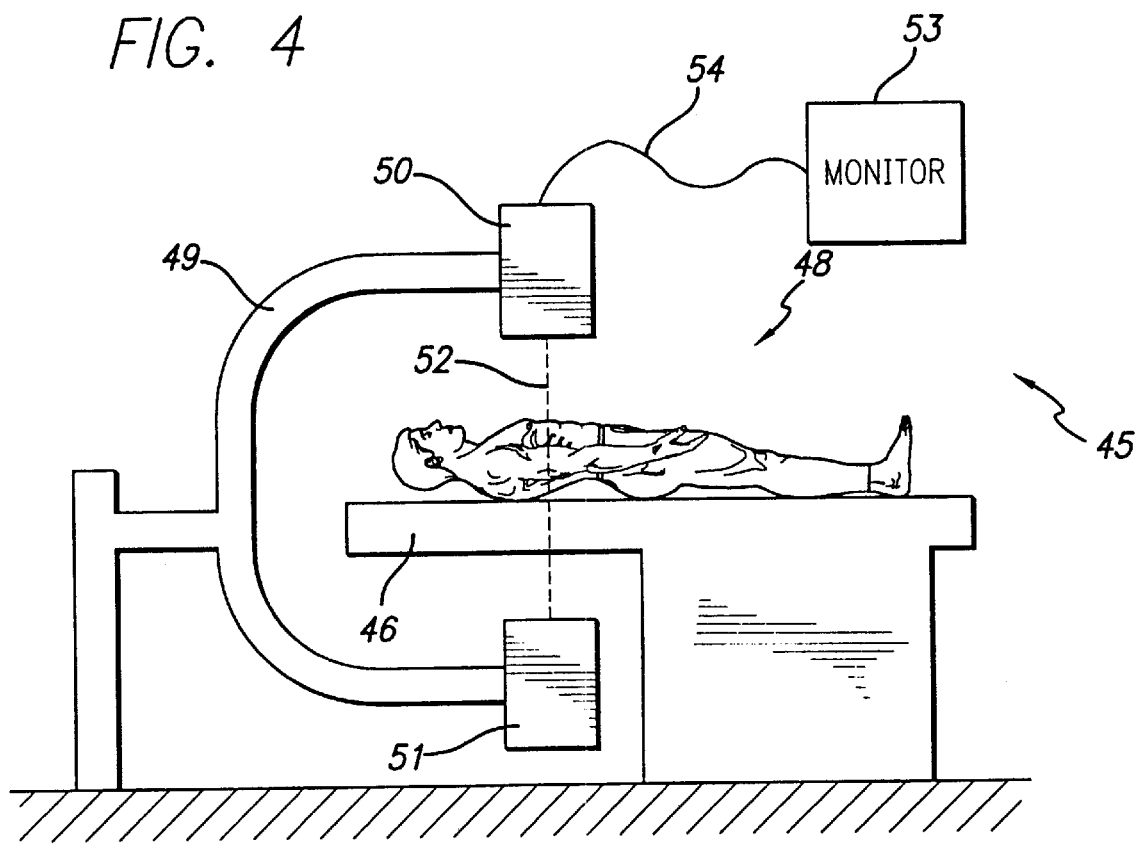
FIG. 4 is a diagram of a machine for fluoroscopically visualizing the spots at injection sites in the heart using the apparatus of FIG. 1 or FIG. 2.

FIG. 4 illustrates a common fluoroscopy system 45, which includes a horizontal platform 46 on which a patient 48 lies. A C-shaped support arm 49 positions a conventional upper X-ray system component 50 and a corresponding conventional lower X-ray system component 51 above and below patient 48. A suitable monitor system 53 coupled by a cable 54 to the X-ray system 50,51 provides continuous monitoring of an image of the radiographic (in this case, fluoroscopic) agent injected into the heart muscle tissue.

Figure 5:
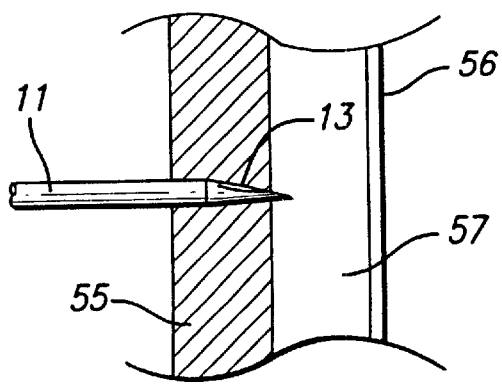
FIG. 5 is a diagram illustrating injection from a needle catheter introduced through the aorta to introduce the tip of a needle on the distal end of the needle catheter through the heart muscle and into the pericardial sac for the purpose of draining the pericardial sac and/or introducing therapeutic substance such as angiogenesis factor or anti-arrhythmic substance into the pericardial sac.

FIG. 5 illustrates an alternate embodiment of the invention in which the tip of needle 13 has been passed all the way through the heart wall 55 into the pericardial space 57 bounded by pericardial membrane 56 and the heart wall 55. (Membrane 57 and space 57 between heart wall 55 constitute the pericardial sac.)

Typically, the treatment substance or apparatus will be introduced to each region of the tissue to be treated through a common outer or sheath catheter, which may or may not have a working well balloon attached to its distal end. In any case, radiographic marking of the treated regions is contemporaneously made with the physical treatment of the tissue thereof, and is radiographically observed as needed so that the physician can readily see which regions of the tissue have been treated and which have not.

In accordance with the present invention, myocardial injection of radiographic contrast agent to create radiographic myocardial marking was performed on three mature swine. A guiding catheter was introduced through a leg artery and its distal tip was positioned in the left ventricle. A small gauge needle catheter was introduced through a guiding catheter into the heart and was used to inject varying amounts of radiographic contrast agent, from 0.1 cubic centimeters to 2 cubic centimeters, directly into the heart muscle at various depths. The needle catheter also was allowed to perforate the heart to inject contrast agent into the pericardium surrounding the heart. Myocardial staining was performed using hand pressure injection of radiographic contrast agent. The catheter then was moved to various sites and the foregoing procedure was repeated at each site, thus creating a radiographic contrast map. The swine were monitored for approximately one hour with intermittent radiography to assess the "time of wash out" of the marked areas.

Also during this procedure, coronary angiography was performed. Radiographic contrast agent was injected into the coronary arteries to visualize the arterial tree in order to compare this with subsequent angiography images to determine if any blood vessels could be visualized. After one month, the swine were returned to the catheterization laboratory. A catheter was introduced through the femoral artery. Coronary angiography again was performed. There was no apparent gross radiographic evidence of blood vessel growth to the previously treated areas. The hearts then were sent for microscopic analysis for evidence of blood vessel growth. Unfortunately, in the preparation process the swine hearts were mishandled and could not be analyzed.

However, my visualization during the sequence of site injections showed that the radiopaque contrast agent remained radiographically viewable by the system of FIG. 3 for durations from one to fifteen minutes, depending on the type and amount of contrast agent used. This appears to be enough time to allow treatment and associated marking of the entire heart, at injection sites located approximately one to two centimeters apart, in approximately fifteen minutes. However, other contrast agents may allow for longer periods, e.g., for an hour. It is noted that the above procedure was performed on normal swine hearts. It is quite possible that if the hearts had been ischemic this "wash-out" period of the contrast agent would have been longer due to reduced blood flow.

Normally, the extent of the treatment around an injection site would extend roughly one to two centimeters radially outward from the injection site. In diseased hearts the myocardial marking may extend outward a different distance from the injection site.

An expected benefit of using radiographic contrast agent to create ischemia/injury is that the degree of injury and the extent thereof may be estimated by the ability to radiographically image the extent of myocardial marking in the in vitro intact heart.

Apart from creation of myocardial ischemia/injury, the technique of the present invention includes injecting a small amount of radiographic contrast agent to "mark" sites of the myocardium of the intact heart to provide a radiographic map for various contemporaneous catheter-based myocardial revascularization techniques, including delivery of laser energy, rf (radio frequency) electromagnetic energy, etc. The radiographic contrast marking of the myocardium of the intact heart provides the operator the opportunity to achieve more effective revascularization of heart muscle tissue by providing a continuous contemporaneous marking of the treated regions, thereby avoiding potential complications such as myocardial perforation by avoiding an already treated region.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention.

What is claimed is:

1. A method for contemporaneously treating a sequence of treatment sites in an internal organ and creating a viewable map of the treated sites, comprising:

(a) advancing a first catheter, having a proximal end and a distal end and a needle attached to the distal end to permit injection of fluid through a guiding catheter, through a body passage and inserting the needle into tissue needing treatment;

(b) injecting contrast substance through the first catheter and needle into a treatment site of the tissue;

(c) controlling treatment of tissue at the treatment site by passing a treatment medium through the first catheter to the tissue at the treatment site;

(d) detecting the extent of migration of contrast substance around the treatment site after injection; and (e) repeating steps (b) through (d) for a plurality of different treatment sites, wherein the detecting indicates where treatment has been performed.

2. An apparatus for contemporaneously treating a sequence of treatment sites in an internal organ and creating a viewable map of the treated sites, comprising:

(a) a first catheter having a proximal end and a distal end for insertion through a body passage to tissue needing treatment;

(b) a needle attached to the distal end of the first catheter to permit injection of fluid into treatment sites of the tissues;

(c) a fluid injection assembly connected in fluid communication with the proximal end of the first catheter and containing contrast substance and treatment substance for contemporaneous injection of the contrast substance and treatment substance into the various treatment sites; and (d) apparatus for detecting the extent of migration of contrast substance around each treatment site after injection, wherein the detecting indicates where treatment has been performed.

3. An apparatus for contemporaneously treating a sequence of treatment sites in an internal organ and creating a viewable map of the treated sites, comprising:

(a) a first catheter having a proximal end and a distal end for insertion through a guiding catheter extending through a body passage to tissue needing treatment;

(b) a needle attached to the distal end of the first catheter to permit injection of fluid into treatment sites of the tissues;

(c) a fluid injection assembly connected in fluid communication with the proximal end of the first catheter and containing contrast substance for injection of the contrast substance into the various treatment sites;

(d) apparatus for detecting the extent of migration of contrast substance around each treatment site after injection, wherein the detecting indicates which treatment sites have been treated; and (e) a treatment device extending through the guiding catheter to a treatment site and a control apparatus coupled to a proximal end of the treatment device for controlling treatment of the tissues contemporaneously with injection of contrast substance into the tissue.

* * * * *